(12) United States Patent
Vince et al.

(10) Patent No.: US 9,169,216 B2
(45) Date of Patent: Oct. 27, 2015

(54) METHOD FOR PREPARATION OF 5-SUBSTITUTED PYRIMIDINES

(75) Inventors: Robert Vince, St. Paul, MN (US); Ashish P. Vartak, St. Paul, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 14/006,171

(22) PCT Filed: Mar. 8, 2012

(86) PCT No.: PCT/US2012/028322
§ 371 (c)(1),
(2), (4) Date: Dec. 30, 2013

(87) PCT Pub. No.: WO2012/128965
PCT Pub. Date: Sep. 27, 2012

(65) Prior Publication Data
US 2014/0121375 A1    May 1, 2014

Related U.S. Application Data

(60) Provisional application No. 61/466,276, filed on Mar. 22, 2011.

(51) Int. Cl.
    C07D 239/26    (2006.01)

(52) U.S. Cl.
    CPC .................................... C07D 239/26 (2013.01)

(58) Field of Classification Search
    CPC ..................................................... C07D 239/26
    USPC ....................................................... 544/335
    See application file for complete search history.

(56) References Cited

U.S. PATENT DOCUMENTS 3,128,312 A * 4/1964 Edgerton ...................... 568/333
4,806,644 A * 2/1989 Elbe et al. ..................... 544/335

FOREIGN PATENT DOCUMENTS

WO    WO-2012/128965 A2    9/2012
WO    WO-2012128965 A2     9/2012

OTHER PUBLICATIONS

Manolikakes, G., Transition-Metal Catalyzed Cross-Coupling Reactions of Functionalized Organometallic Reagents of Organozinc Reagents, Dissertation, LMU Munchen, 255 pages, (2008).*
West, Anthony R., Solid State Chemistry and Its Applications, Wiley, New York, 1988, 358.*
"International Application Serial No. PCT/US2012/028322, International Search Report mailed Jun. 21, 2012", 3 pgs.
"International Application Serial No. PCT/US2012/028322, Written Opinion mailed Jun. 21, 2012", 6 pgs.
Manolikakes, "Transition-Metal Catalyzed Cross-Coupling Reactions of Functionalized Organometallic Reagents, Nickel-Catalyzed Amination of Aryl Chlorides and Preparation and Reactions of Organozinc Reagents.", [Online]. Retrieved from the internet: <http://edoc.ub.uni-muenchen.de/13992/1/Manolikakes_Georg.pdf>, (2008).
Molander, "Aminomethylations via Cross-Coupling of Potassium Organotrifluoroborates with Aryl Bromides", Org Lett., 2007. vol. 9 (8), pp. 1597-1600, [Online]. Retrieved from the internet: <http://www.ncbi.nlm.nih.gov/pmc/articles/PMC2515366/pdf/nihms60277.pdf>, (2007), 7 pgs.
"International Application Serial No. PCT/US2012/028322, International Preliminary Report on Patentability mailed Mar. 27, 2014", 8 pgs.
"International Application Serial No. PCT/US2012/028322, International Search Report mailed Jun. 21, 2012", 2 pgs.
Manolikakes, Georg, "Transition-Metal Catalyzed Cross-Coupling Reactions of Functionalized Organometallic Reagents, Nickel-Catalyzed Animation of Aryl Chlorides and Preparation and Reactions of Organozinc Reagents.", Dissertation, LMU München. [online]. Retrieved from the internet: <http://edoc.ub.uni-muenchen.de/13992/1/Manolikakes_Georg.pdf>, (2008), 255 pgs.
Molander, Gary A., et al., "Arminomethylations via Cross-Coupling of Potassium Organotrifluoroborates with Aryl Bromides", *Org Lett.*, 9(8), 1597-1600 [online]. Retrieved from the Internet: <http://www.ncbi.nlm.nih.gov/pmc/articles/PMC2515366/pdf/nihms60277.pdf>, (2007), 9 pgs.

* cited by examiner

*Primary Examiner* — Erich A Lesser
(74) *Attorney, Agent, or Firm* — Schwegman Lundberg & Woessner, P.A.

(57) ABSTRACT

The present invention provides a method to prepare 5-substituted pyrimidines by reacting a 5-acylpyrimidine with a suitable nucleophile to afford a 5-methanolpyrimidine, such as flurprimidol.

20 Claims, No Drawings

METHOD FOR PREPARATION OF 5-SUBSTITUTED PYRIMIDINES

CROSS-REFERENCE TO RELATED APPLICATIONS

This application is a U.S. National Stage Application filed under 35 U.S.C §371 of International Application Serial No. PCT/US2012/028322, filed on Mar. 8, 2012 and published as WO 2012/128965 A2 on Sep. 27, 2012, which application claims priority to U.S. Provisional Patent Application Ser. No. 61/466,276 filed Mar. 22, 2011, which applications are incorporated herein by reference in their entirety.

BACKGROUND OF THE INVENTION

The 5-pyrimidinemethanol, flurprimidol (1, α-isopropyl-α-[p-(trifluoromethoxy)phenyl]-5-pyrimidinemethanol, CAS #56425-91-3) is a plant-growth regulator currently marketed under the brand names Cutless® and Topflor® as well as a mixture with various other agrochemicals. In the United States, it is manufactured by SePRO Corporation (Carmel, Ind.). Flurprimidol was first described in U.S. Pat. No. 3,967,949. Its structure is depicted below:

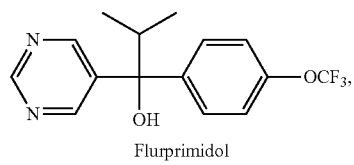

Flurprimidol

Flurprimidol (1) is currently manufactured by the methodology illustrated in Scheme 1.

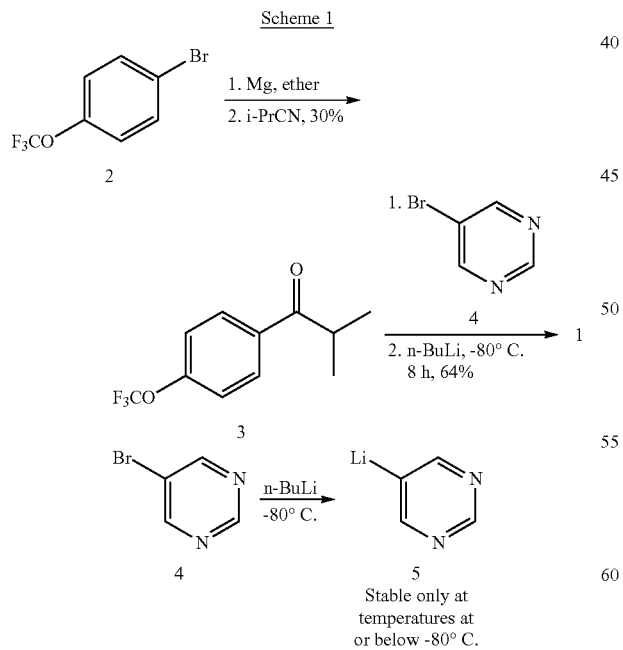

Briefly, p-(trifluoromethoxy)bromobenzene (2) is converted to p-(trifluoromethoxy) phenylmagnesium bromide and reacted with isobutyronitrile to afford isopropyl p-(trifluoromethoxy)phenyl ketone (3). The reaction of 3 with 5-bromopyrimidine 4 in the presence of n-BuLi affords 1. This reaction proceeds through the intermediacy of the lithiated intermediate 5. The conversion of 5-bromopyrimidine (4) to the 5-lithiopyrimidine (5) occurs without significant degradation only at or below −80° C. The cryogenic operation required to maintain such reaction conditions is expensive. The limited stability of 5 mandates the presence of 3 during the addition of n-butyllithium, which introduces impurities such as 6 and 7 in the final product.

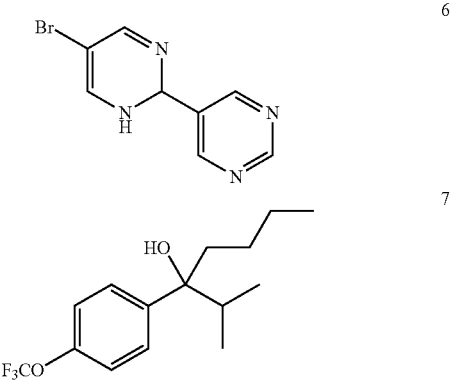

SUMMARY OF THE INVENTION

The present invention provides a method for preparing 5-acylpyrimidines comprising:

(a) reacting a compound of formula (II):

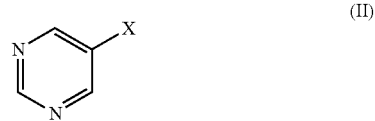

(II)

wherein X is halo or a sulfonate leaving group, such as tosyl or mesyl, with a compound of formula (III), (IV) or (V):

$R^1CH_2MX$      (III), $(R^1CH_2)B(Y)_2$      (IV), $(R^1CH_2)(Li^+)_x(M^{++})_y(X^-)_z$      (V)

wherein $R^1$ is an organic group, M is a suitable metal cation, Y is $(C_1-C_4)$alkoxy, each X is halo, and x, y and z are selected so that the net charge on compound (V) is 0, in the presence of an effective catalytic amount of a complexed metal, to yield a compound of the formula (VI):

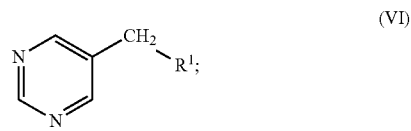

(VI)

and (b) oxidizing compound (VI) to yield compound (VII):

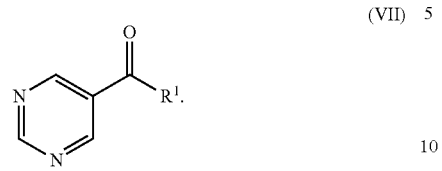

(VII)

The present invention also comprises the step of reacting compound (VII) with a suitable nucleophile, such as $(R^2)MX$ or $(R^2)_2M$ wherein $R^2$ is an organic group, M is a single metal cation or a mixed metal cation and X is halo, or mixed halo, to yield a 5-methanolpyrimidine compound of formula (I):

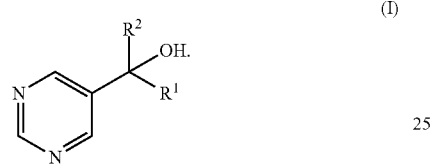

(I)

Such compounds include the fungicides and/or plant growth retardants flurprimidol ($R^1$=4-trifluoromethoxyphenyl, $R^2$=isopropyl), ancymidol ($R^1$=4-methoxyphenyl, $R^2$=cyclopropyl), fenarimol ($R^1$=4-chlorophenyl, $R^2$=2-chlorophenyl), triarimol ($R^1$=phenyl, $R^2$=3,4-dichlorophenyl), and nuarimol ($R^1$=4-fluorophenyl, $R^2$=2-chlorophenyl).

Novel 5-acylpyrimidine intermediates (VII) employed in the synthesis are also within the scope of the invention, as are other useful 5-methanolpyrimidines of general structure (I), and uses therefore. Such uses include plant growth control/limitation of plants such as turfgrass and ornamental trees and shrubs, as well as herbicides.

Thus, the present invention also includes 5-substituted pyrimidines of formula (IX):

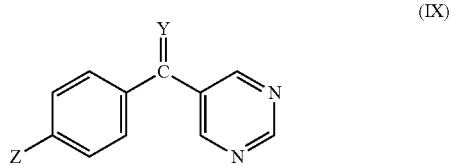

(IX)

wherein Y is O or $(H)_2$, and Z is $(C_1-C_4)$trifluoroalkyl, $(C_1-C_4)$alkoxy or halo, including compounds 8, 12, 18 and 23.

DETAILED DESCRIPTION OF THE INVENTION

The present invention provides a means to bypass the problematic chemical transformations in the currently-utilized method for 5-methanolpyrimidine synthesis. Shown in Scheme 2, for the retro-synthesis of flurprimidol, the sequence of alkyl group introduction is altered so that a 5-metallopyrimidine intermediate is not necessary. For example, the ketone intermediate necessary for an improved method to prepare flurprimidol (1) is 4-trifluoromethylphenyl-5-pyrimidyl ketone (8), wherein (isopropyl)M (9) can be isopropyl lithium, an isopropyl Grignard reagent, and the like.

Scheme 2

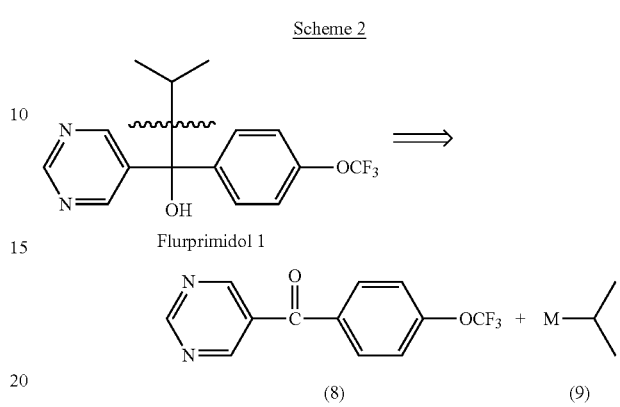

(8) (9)

Therefore, the synthetic route of the present invention begins with a novel synthesis of a 5-acylpyrimidine VII. Ketone VII is then reacted with a suitable nucleophile, such as (9) to afford a 5-methanolpyrimidine such as flurprimidol. Traditionally, such transformations have been inefficient due to enolization of the ketone and free-radical mediated reduction of the C=O bond, both reducing yields. However, the Grignard reagent in a suitable organic solvent such as THF or an ether, can be mixed with one equivalent of LiCl and, subsequently, 50-100 mol-% $ZnCl_2$ or other metal halide as discussed below to form the lithium complex of a magnesiozincate which appears to possess much reduced basicity and therefore leading to nucleophilic attack as the predominant reaction pathway.

The present method comprises the following steps:

Step 1

A transition-state metal mediated C—C bond coupling between a 5-sulfonyl or halopyrimidine (II) and an appropriate organometallic or organoboron reagent (III) to afford a 5-substituted pyrimidine (VI);

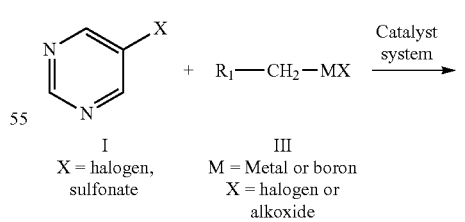

I
X = halogen, sulfonate

III
M = Metal or boron
X = halogen or alkoxide

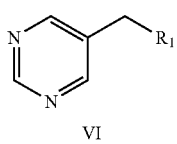

VI

Step 2

Oxidation of the activated benzylic carbon of VI to afford a 5-acylpyrimidine (VII); and

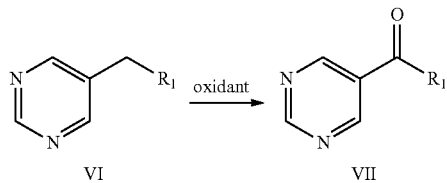

Step 3

Addition of a nucleophile to the ketone to afford the target pyrimidinemethanol (I)

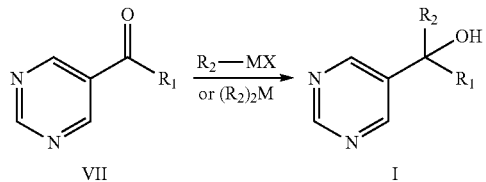

Step 1. Synthesis of III and IV

Compound III can be an organometallic reagent with the metal being Mg(II), Zn(II), Mn(II), Cu(I), Sn(IV) or Li(I). Compound IV can also include mixed organometallic complexes such as $R_1CH_2(Li^+)_x(M^{++})_yX^-_z$ (where x, y and z are such that the net charge of the species=0); for example, if $M^{++}$ is zinc, the mixed metal complex is lithium zincate.

Preparation of compounds III or IV can be accomplished through one of the following methods.

Method 1) An alkyl halide $R_1CH_2X$ is reacted with a suitable form of a metal in an inert solvent at a temperature range between $-20°$ C. and $90°$ C. An activating agent such as $I_2$ or dibromoethane may be added. This procedure affords $R_1CH_2MX$.

Method 2) An alkyl halide $R_1CH_2X$ is reacted as per Method 1, except that LiCl is mixed with the metal in an inert solvent before addition of the alkyl halide. This procedure affords $R_1CH_2M(Li)XCl$. LiCl may be substituted with LiBr or LiI.

Method 3) An alkyl halide $R_2CH_2X$ is treated with an organometallic reagent such as n-BuLi, s-BuLi, t-BuLi or i-PrMgX in the presence of a complexing agent such as tetramethyl ethylenediamine (TMEDA). Additives such as $MgX_2$ or $ZnX_2$ may be added to generate a mixed organometallic reagent.

A "suitable form of metal" is a form that reacts with $R_2CH_2X$ to preferentially afford $R_2CH_2MX$, comprising a "suitable metal cation," over the Würtz coupling product, $R_2CH_2CH_2R_2$. For example, commercial zinc dust reacts with 4-($OCF_3$)BnBr to afford 80% of (4-($OCF_3$)-$PhCH_2$)$_2$ and is hence an unsuitable form of zinc. When the zinc dust is heated with $I_2$ (1 wt %) and dibromoethane (2 wt %) in THF at reflux until ethylene gas evolves, the resulting active form of zinc dust reacts with 4-($OCF_3$)BnBr to afford >98% of 4-($OCF_3$)BnZnBr.

The catalyst utilized for the coupling of compounds III, IV or V with II may be derived from palladium, nickel or iron in any oxidation state. Examples are $(Ph_3P)_4Pd$, $(Ph_3P)_2PdCl_2$, $(Ph_3P)_2NiCl_2$ and $Fe(acac)_2$. Catalyst loading is from 0.1 to 10 mol % of II. The reaction temperature ranges from $-10°$ C. in case of palladium complexes to room temperature in case of the nickel and iron complexes. Reaction time is between 48 h for the palladium-catalyzed reactions to 15 minutes for the nickel-catalyzed reaction. Precise conditions, solvents, method of isolation and yields are given in Table 1. In all cases, the reaction can be quenched with saturated aqueous $NH_4Cl$, washed with sat. $NaHCO_3$, the organic layer dried with $MgSO_4$ and evaporated to a pale yellow to brown gum, which was in all cases found to be >95% pure VI by NMR and carried to Stage 2 without further purification. Table 1 describes the yields obtained with specific conditions and catalysts.

TABLE 1

| | | | | | | | | |
|---|---|---|---|---|---|---|---|---|
| Entry | (III) | (II) | Additive 100 mol % | Catalyst | Cat Mol % | Solvent | T (° C.) | Time (hours) | Yield (VI) |
| 1 | $R_1$-MgBr* | 5-bromo | LiCl | $(Ph_3P)_4Pd$ | 5 | THF | rt | 8 | ca.20% |
| 2 | $R_1$-MgBr* | 5-bromo | $ZnCl_2$ | $(Ph_3P)_4Pd$ | 5 | THF | rt | 24 | 46% |
| 3 | $R_1$-MgBr* | 5-bromo | $ZnCl_2$ | $(Ph_3P)_4Pd$ | 5 | THF | 0 | 24 | 40% |
| 4 | $R_1$-ZnBr* | 5-bromo | No | $(Ph_3P)_4Pd$ | 5 | THF | 0 to rt | 24 | 73% |
| 5 | $R_1$-ZnBr* | 5-bromo | LiCl | $(Ph_3P)_4Pd$ | 5 | THF | rt | 4 | 90% |
| 6 | $R_1$-ZnBr* | 5-bromo | LiCl | $(Ph_3P)_2NiCl_2$ | 5 | THF | rt | 0.25 | 95% |
| 7 | $R_1$-ZnBr* | 5-bromo | LiCl | $(Ph_3P)_2NiCl_2$ | 0.5 | THF | rt | 1 | 98% |
| 8 | $R_1$-ZnBr* | 5-bromo | LiCl | $(Ph_3P)_2NiCl_2$ | 0.1 | THF | rt | 2 | 93% |
| 9 | $R_1$-ZnBr* | 5-iodo | LiCl | $(Ph_3P)_2NiCl_2$ | 0.1 | THF | rt | 2 | 85% |
| 10 | $R_1$-ZnBr* | 5-chloro | LiCl | $(Ph_3P)_2NiCl_2$ | 0.1 | THF | rt | 24 | 12% |
| 11 | $R_1$-ZnBr* | 5-bromo | LiCl | $Fe(acac)_2$ | 5 | THF | rt | 48 | 35% |
| 12 | $R_1$-ZnBr* | 5-bromo | LiCl | $Fe(acac)_2$ | 10 | THF | Rt | 48 | 28% |
| 13 | $R_1$-ZnBr* | 5-bromo | LiCl | $Fe(acac)_2$ | 10 | DME | 90 | 3 | 74% |
| 14 | $R_1$-ZnBr* | 5-bromo | LiCl | $Fe(acac)_2$ | 1 | DME | 90 | 3 | 88% |
| 15 | $R_1$-ZnBr* | 5-bromo | No | $(Ph_3P)_2NiCl_2$ | 0.1 | THF | rt | 14 | 71% |
| 16 | $R_1$-ZnBr* | 5-bromo | LiCl | $(Ph_3P)_2NiCl_2$ | 0.1 | Ether | rt | 2 | 94% |
| 17 | $R_1$-ZnBr* | 5-bromo | LiCl | $(Ph_3P)_2$ | 0.1 | di-n-bu ether | Rt | 48 | NR |
| 18 | $R_1$-ZnCl* | 5-bromo | LiCl | $(Ph_3P)_2NiCl_2$ | 0.1 | THF | Rt | 5 | 88% |
| 19 | $R_1$-ZnCl† | 5-bromo | LiCl | $(Ph_3P)_2NiCl_2$ | 0.1 | THF | 0° C. | 5 | 54% |

TABLE 1-continued

Conditions scan for stage 1.

| Entry | (III) | (II) | Additive 100 mol % | Catalyst | Cat Mol % | Solvent | T (° C.) | Time (hours) | Yield (VI) |
|---|---|---|---|---|---|---|---|---|---|
| 20 | $R_1$-ZnCl‡ | 5-bromo | LiCl | $(Ph_3P)_2NiCl_2$ | 0.1 | THF | 0° C. | 5 | 99% |
| 21 | $R_1$-ZnCl‡ | 5-bromo | LiCl | $(Ph_3P)_2NiCl_2$ | 0.1 | THF | 0° C. | 5 | 92% |

\*$R_1$ = 4-trifluoromethoxyphenyl,
†$R_1$ = 4-methoxyphenyl,
‡$R_1$ = 4-chlorophenyl.
Yields refer to isolated yields.
LiCl was dried under hyvac for 15 min at 150° C.
$ZnCl_2$ was melted under hyvac and congealed with vigorous shaking to afford a dry powder.
Zn dust was heated with $I_2$ (1 wt %) and dibromoethane (2 wt %) at reflux in the solvent until ethylene gas evolved and then cooled to rt before use for formation of $R_1$-ZnX.

Nickel(II)chloride (as its bis-triphenylphosphine complex) is a surprisingly active catalyst for this particular benzylic $sp^3$-aryl $sp^2$ coupling reaction. An organozincate, prepared in the absence of magnesium(II) is the most suitable benzylic coupling partner. The nickel(II) catalyst may be substituted with $Fe(acac)_2$, but the reactions requires higher temperature (and therefore change of solvent to DME) to go to completion. Palladium catalysts are also active, but are impractical due to their cost (2000-times more expensive than nickel catalysts). Diethyl ether is also a suitable solvent for the reaction. When the stoichiometry of reactants II and III is held in strict 1:1 stoichiometry, the oily residue after workup is essentially pure VI with only traces of the Würtz coupling product described earlier. The residue is utilized directly for the oxidation in Step 2. In case the stoichiometry is not rigidly 1:1, the presence of traces of II and III do not affect the outcome of the manipulations in Step II.

Step 2. Oxidation of VI to Pyrimidyl Ketone (VII)

The benzylic methylene of compound VI is susceptible to oxidation. This oxidation may be conducted utilizing a number of known oxidizing agents. The oxidant may be a sole, stoichiometric oxidant, such as $SeO_2$, $KMnO_4$ and $CrO_3$, or may be a catalytic oxidant combined with a 'sacrificial' oxidant, such as the combination of $SeO_2$ and t-butylhydroperoxide, N-hydroxyphthalimide and t-butyl hydroperoxide, $RuO_2$ and commercial bleach. Alternatively, benzylic halogenations may be effected with NBS (N-bromosuccinimide), NCS(N-chlorosuccinimide), $Br_2$, chloramine-T, etc. in the presence or absence of a radical initiator like azobisisobutyronitrile (AIBN), dibenzoylperoxide and irradiation with any suitable wavelength of light. The halogenated products are carried forward into an oxidation, for example, with nitric acid in AcOH, which affords the ketone VII.

Amongst stoichiometric oxidants, $KMnO_4$ is an oxidant of choice because of its low cost and the environmentally benign nature of the $MnO_2$ by-product. Conditions for $KMnO_4$ oxidation are tailored to the reactivity of the 5-substituted pyrimidine VI. For example, while a temperature of 80° C. is required for the oxidation of 4-(trifluoromethoxy)benzyl substituted VI, the oxidation of 4-(methoxy)substituted VI occurs at room temperature. A suitable organic solvent such as ethyl acetate may be optionally employed, but is not necessary.

After consumption of VI, the reaction mixture is extracted with a solvent such as ethyl acetate and the organic layer can be washed with dilute sodium bisulfite, brine, dehydrated and evaporated. The residue is utilized directly in Step 3.

Step 3. Conversion of Acylpyrimidine (VII) to Pyrimidinemethanol (I)

The reaction of nucleophiles such as organolithiums ($R_2Li$) and organomagnesiums ($R_2MgX$) with 5-acylpyrimidines such as VII occurs in low yields (<10%). Competing reactions are enolization leading to recovery of VII after workup and β-hydride transfer leading to recovery of VIII after workup.

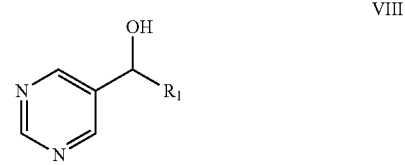

VIII

To obtain maximal conversion of VII to I, the reactivity of the nucleophile is modulated by the addition of LiCl and 50-100 mol % of either $ZnX_2$, $MnX_2$, $LnX_3$ where Ln is a lanthanide and X is halo, preferably chloro. The effective nucleophile in such as case may be represented as $(Li(R_2—ZnX)MgX_2)_y$.solvate$_z$, where the solvent is an ether such as THF or diethyl ether and where y and z are such that all the low-lying d-orbitals of the transition metal are filled.

When duly optimized, a 100% conversion of VII can be obtained and the isolated yield is as high as 98%. Isolation of I can be effected by extraction of the reaction mixture of Step 3 with saturated aqueous $NH_4Cl$, evaporation of the organic layer and recrystallization of the semisolid residue from a suitable solvent or solvent combination.

EXPERIMENTAL SECTION

Example 1

Synthesis of Flurprimidol

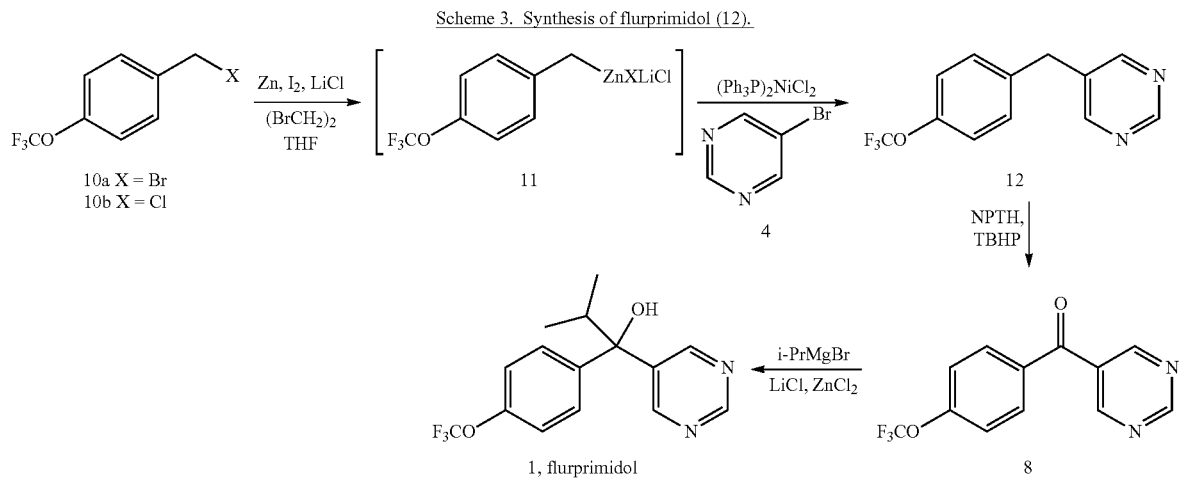

Scheme 3. Synthesis of flurprimidol (12).

Stage 1. Synthesis of 5-[4-(trifluoromethoxy)benzyl]pyrimidine (12)

(A) From 4-(trifluoromethoxy)benzyl bromide (10a)

A suspension of zinc dust (15 g, excess) in THF (100 mL) was treated with LiCl (10.00 g, 238 mmol) and 1,2-dibromoethane (0.5 mL, catalytic). The warm mixture thus formed was treated dropwise with a solution of 4-(trifluoromethoxy)benzyl bromide (10a) (50.00 g, 209 mmol) in THF (200 mL) over a period of 3 hours. The resulting mixture was stirred for an additional hour, affording a solution of the lithium zincate 11, and then treated with $(Ph_3P)_2NiCl_2$ (300 mg, 0.1 mol or 0.001 equivalents). The red suspension was treated drop wise with a solution of 5-bromopyrimidine (4) (33.23 g, 200 mmol) in THF (50 mL) over a period of one hour. The mixture was stirred for another 10 minutes and then poured into 300 mL of saturated aq. $NH_4Cl$. The aqueous layer was washed with 200 mL of THF-ether (1:1), the combined organic layers washed with saturated aqueous $NaHCO_3$, filtered, dried ($MgSO_4$) and evaporated under reduced pressure to afford a pale yellow oily residue weighing 51.00 g (96%) and was found to be pure 5-[4-(trifluoromethoxy)benzyl]pyrimidine (12). $^1H$ NMR (400 MHz, $CDCl_3$) δ ppm 9.26 (s, 1H, pyrimidine), 8.84 (s, 2H, pyrimidine), 7.19 (s, 4H, Ar, no para-pattern observed), 4.06 (s, 2H, methylene); $^{13}C$ NMR (100 MHz, $CDCl_3$) 156.3, 157.1, 147.4, 139.6, 134.8, 131, 121.7, 35.0. ESI-MS (low-res) 255.0 $(M+H)^+$.

(B) From 4-(trifluoromethoxy)benzyl chloride (10b)

To zinc dust (1.30 g, 20 mmol) in THF (20 mL) was added $I_2$ (10 mg) and dibromoethane (100 mg). The suspension was heated to reflux and then cooled to rt before being treated with 10b. The resulting suspension was heated to reflux for 6 h and then cooled to rt. An iodine titration indicated 94% yield of the organozinc reagent. $(Ph_3P)_2NiCl_2$ (50 mg, cat) was added resulting in a bright red suspension, which was treated with 4 (2.97 g, 18.8 mmol), resulting in discharge of the red color. The mixture was extracted with $NH_4Cl$, saturated $NaHCO_3$ and the organic layer was evaporated under reduced pressure to afford a pale yellow oily residue (4.4 g, 92%) which was found to be pure 12.

Step 2. Synthesis of 4-trifluoromethoxyphenyl-5-pyrimidyl ketone (8)

(A) by NBS and Nitric Acid-AcOH Mediated Oxidation

To a solution of 12 (25.00 g, 98.4 mmol) in EtOAc (55 mL) was added NBS (17.8 g, 100 mmol). The mixture was flushed with argon gas and then irradiated with a 300 W tungsten-filament lamp for 90 minutes, during which, all of IV was consumed according to TLC ($R_f$ of IV=0.35 in $CH_2Cl_2$-EtOAc, 3:1). The mixture was washed thrice with water (20 mL), dried, and evaporated to afford a crude brown oil weighing 35 g (108% mass recovery). The crude gum was dissolved in AcOH (50 mL) and nitric acid (25 mL) was added. The mixture was heated at 50° C. until evolution of a brown gas completely ceased, and the poured into 10% aq. sodium chloride and 20 g of ice. The mixture was extracted with EtOAc (50 mL, 3x), the EtOAc extracts dried ($MgSO_4$) and evaporated to a brown gum. This gum was triturated with hexanes (100 mL) to afford a brown solid, which was stirred in boiling hexanes-EtOAc-EtOH (10:1:1, 200 mL) until complete solution occurred. The solution was allowed to cool in the refrigerator overnight and the needles formed were filtered, crushed, and dried under vacuum to afford pure 8 (15.71 g, 60%). The filtrates contained negligible amounts of V. mp=56-58° C.; $^1H$ NMR (400 MHz, $CDCl_3$) δ ppm 9.18 (s, 1H, pyrimidine), 9.02 (s, 1H, pyrimidine), 7.40 (d, 2H, Ar), 7.18 (d, 2H, Ar). $^{13}C$ NMR (100 MHz, $CDCl_3$) δ ppm 213.8 (ketone) 158.2, 156.1 (pyrimidine), 136.4, 136.1, 135.0, 127.9, 121.8 (Ar).

(B) By N-hydroxyphthalimide and tert-butylhydroperoxide mediated oxidation

A solution of 12 (2.54 g, 10 mmol) in tert-butyl hydroperoxide (10 mL) was treated with N-hydroxyphthalimide (10 mg, catalytic). The mixture was irradiated with 300 W lamp while being cooled in an ice-water bath. After 6 h, the mixture was evaporated under reduced pressure and partitioned between EtOAc and brine. The EtOAc layer was treated with activated charcoal, filtered and evaporated under reduced pressure. The residue was triturated with hexanes:ether (2:1) and the supernatant was decanted and evaporated to afford 8 as an oil (2.60 g, 98% yield). The white solid left behind after trituration was found to be mostly N-hydroxyphthalimide.

(C) By $KMnO_4$ Mediated Oxidation

To solution of 12 (2.54 g, 10 mmol) in EtOAc (10 mL) was added water (20 mL) and $KMnO_4$ (6.32 g, 40 mmol). The mixture was heated to reflux for 1 h and then filtered through celite. The organic layer was evaporated under reduced pressure to afford an oil (2.40 g, 88%) that was found by NMR to be pure 8.

equiv), followed by commercial isopropyl magnesium chloride (2M in THF, 26.6 mL) dropwise at 0° C. The mixture was stirred for an extra 30 minutes and then extracted with sat. aq. $NH_4Cl$ (25 mL, 2×). The organic layer was evaporated to a pale yellow gum, which was dissolved in toluene (10 mL) and hexane (10 mL). This solution upon cooling in the refrigerator afforded white needles. Hexane (30 mL) was added to complete crystallization (TLC of the mother-liquor showed absence of 1) and the filtered. The cake was dried in air until constant weight and was found to be pure flurprimidol (1). The yield was 15.14 g (94%). M.p.=95-97° C.; $^1$H NMR (600 MHz, $CDCl_3$) δ ppm 9.06 (s, 1H, ar), 8.82 (s, 1H, Ar), 7.52 (d, 2H, J=1.8 Hz, Ar), 7.19 (d, 2H, J=1.9 Hz, Ar), 2.86 (dq, 1H, $J_1$=5.7 Hz, $J_2$=4.3 Hz, CH), 0.93 (d, 6H, J=4.5 Hz, $(CH(CH_3)_2)$. $^{13}$C NMR (125 MHz, $CDCl_3$) δ ppm 157.0, 154.6, 143.41, 138.9, 127.1, 121.0 (Ar), 78.34 (C), 35.0 (CH), 16.8, 16.6 $(CH(CH_3)_2)$.

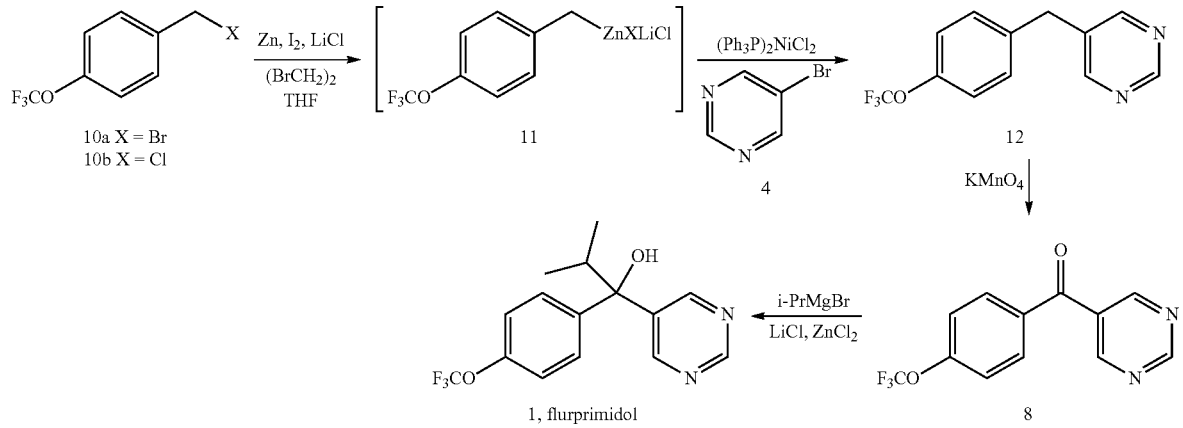

Step 3. Conversion of 5-acylpyrimidine 8 to flurprimidol 1

A solution of 8 (14.0 g, 53.23 mmol) in THF (100 mL) was treated with LiCl (2.23 g, 53.23 mmol), $ZnCl_2$ (3.61 g, 0.5

Example 2

Synthesis of Ancymidol (15)

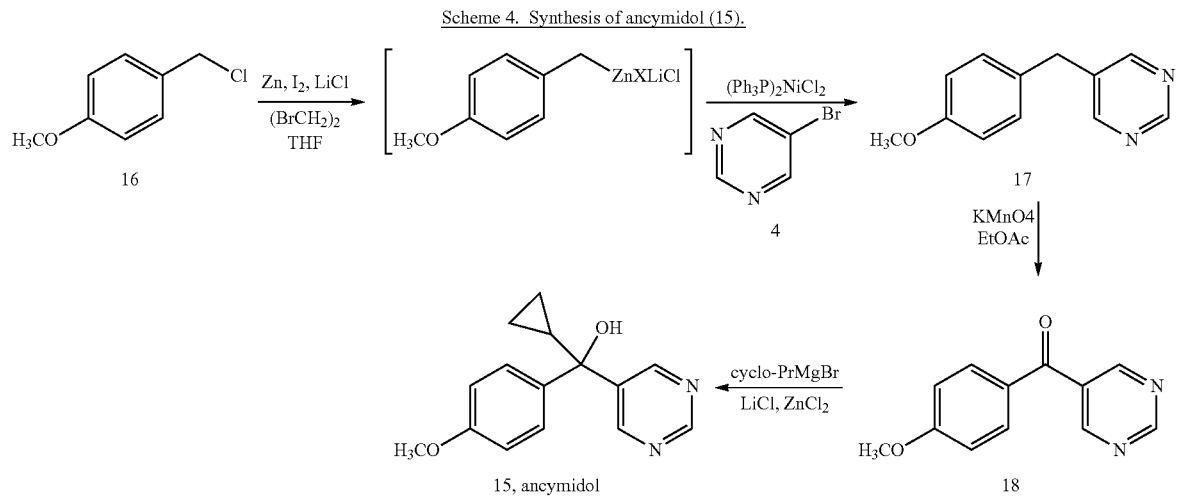

Step 1. Synthesis of 4-(methoxybenzyl)pyrimidine (17)

A suspension of zinc dust (1300 mg, 20 mmol), LiCl (420 mg, 10 mmol), I₂ (10 mg), dibromoethane (50 mg) in THF (20 mL) was heated to reflux for 15 min. and then treated with 4-methoxybenzyl chloride (16) (1.56 g, 10 mmol). Heating was continued for 6 h and the suspension was then cooled to tered and dried to afford 374 mg (31%) of 15 as a white solid. Mp=108-110° C.; $^1$H NMR (300 MHz, CDCl₃) δ ppm 9.06 (s, 1H), 8.48 (s, 2H), 7.82 (d, 2H), 7.03 (d, 2H), 3.99 (s, 3H), 1.08 (m, 1H), 0.50-0.31 (m, 4H).

Example 3

Synthesis of Fenarimol (19)

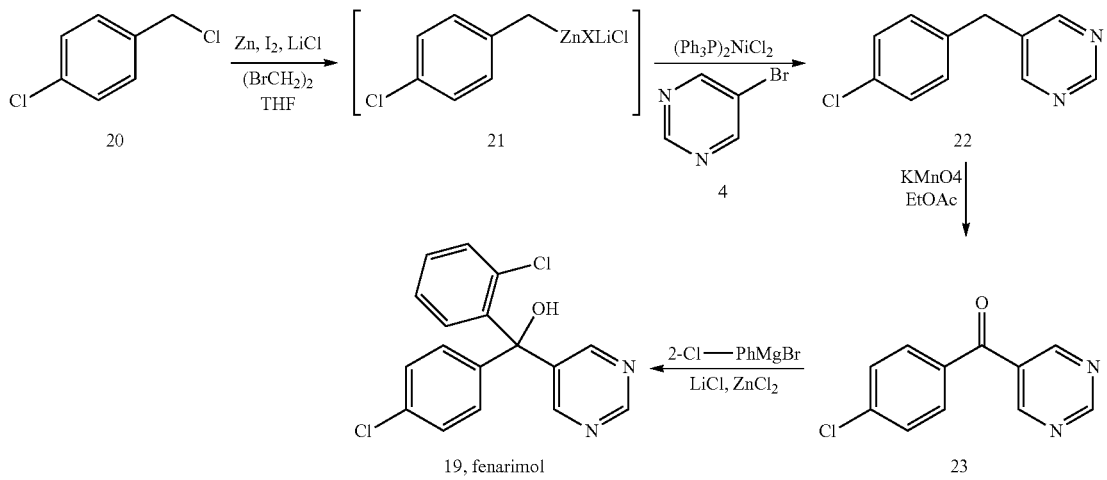

Scheme 5. Synthesis of fenarimol (19)

rt before being treated (Ph₃P)₂NiCl₂ (50 mg). The resulting red suspension was treated with 4 (1.56 g, 10 mmol) and the mixture was stirred for an extra 10 min. before being washed with NH₄Cl and saturated NaHCO₃. The organic layer was evaporated under reduced pressure to afford a pale yellow oil (3.03 g, 94%), which was found to be pure 17 by NMR. $^1$H NMR (300 MHz, CDCl₃) δ ppm 9.01 (s, 1H), 8.55 (s, 2H), 7.95 (d, 2H), 7.39 (d, 2H), 4.12 (s, 2H), 3.52 (s, 3H).

Step 2. Synthesis of 4-(methoxybenzyl)-5-pyrimidyl ketone (18)

A solution of 17 (2.00 g, 10 mmol) in EtOAc (10 mL) was treated with KMnO₄ (3.18 g, 20 mmol) in water (20 mL). The biphasic mixture was stirred at rt for 12 h, at which point the purple color was discharged. The mixture was filtered through celite and the organic layer was evaporated to afford 18 as an oil (2.04 g, 94%). $^1$H NMR (300 MHz, CDCl₃) δ ppm 9.78 (s, 1H), 9.14 (s, 2H), 7.83 (d, 2H), 7.08 (d, 2H), 3.74 (s, 3H). $^{13}$C NMR (75 MHz, CDCl₃) δ ppm 194.3, 158.3, 158.0, 138.5, 136.6, 128.4, 118.0, 116.8, 63.1.

Stage 3. Synthesis of Ancymidol (15)

To a solution of cyclopropylmagnesium bromide (0.5 M in THF, 9 mL, 4.5 mmol) was added ZnCl₂ (612 mg, 4.5 mmol) and LiCl (0.189 mg, 4.5 mmol). To this clear yellow solution was added 18 (1.00 g, 4.5 mmol) in THF and the mixture was stirred for 4 h at rt before being washed with sat. NH₄Cl. The organic layer was diluted with EtOAc and washed with sat. NaHCO₃ before being dried and evaporated to a brown gum, which was dissolved in toluene and poured over a plug of silica gel (20 g). The plug was washed with hexane-EtOAc (100 mL). The eluants were evaporated to a yellow oil that solidified upon trituration with hexanes. The solid was fil-

Step 1. Synthesis of 5-(4-chlorobenzyl)pyrimidine (22)

A mixture of Zn dust (13 g, 100 mmol), LiCl (4.2 g, 100 mmol), I₂ (250 mg), dibromoethane (2.5 g) in THF (100 mL) was heated to reflux for 15 min. and then treated with 4-chlorobenzyl chloride (8.1 g, 50 mmol). The suspension was heated to reflux for 48 h and then cooled to rt. An iodometric titration indicated a 65% yield of the zincate. (Ph₃P)₂NiCl₂ (200 mg) was then added and the red suspension treated with 4 (5.13 g, 32.5 mmol). After 30 min, the pale green suspension was extracted with sat. NH₄Cl (200 mL), diluted with EtOAc (300 mL) and extracted with sat. NaHCO₃ (200 mL). The organic layer was evaporated under reduced pressure to afford a semisolid weighing 6.07 g (60% yield) that was identified by NMR to be 22 and the "homocoupled" product, 1,2-di-(4,4'-dichloro)phenyl ethane in a 3:2 ratio. This residue was directly subjected to Step 2 without further purification.

Step 2. Synthesis of 4-chlorophenyl-5-pyrimidyl ketone (23)

A mixture of the residue of Step 1 containing 22 (5.00 g, 5 mmol based on NMR purity), EtOAc (50 mL), water (100 mL) and KMnO₄ (5 g, excess) was heated to reflux for 6 h and then filtered through celite. The filtrate was diluted with brine (50 mL) and the organic layer was separated, washed with 5% sodium bisulfate, sat. NaHCO₃ (50 mL, 3 times) and evaporated to a tan solid. This solid was stirred in hexanes and then filtered to afford pure 23 as an off-white solid. (4.5 g, 85%) Mp=88-90° C.; $^1$H NMR (300 MHz, CDCl₃) δ ppm 9.81 (s, 1H), 9.20 (s, 2H), 7.92 (d, 2H), 7.26 (d, 2H); $^{13}$C NMR (75 MHz, CDCl₃) δ ppm 190.4, 158.6, 158.1, 138.4, 132.1, 127.5, 118.7, 118.0.

Step 3. Synthesis of fenarimol (19)

To a suspension of magnesium turnings (1.00 g, excess) in THF (20 mL) was added 1,2-dibromoethane (0.05 mL). After 5 min, o-bromochlorobenzene (960 mg, 5 mmol) was added in one portion, causing slight warming as the oxidative addition initiated. After 90 min. a menthol-phenanthroline titration of this solution indicated 100% insertion. This grey solution was treated with $ZnCl_2$ (680 mg, 5 mmol) and then with 23 (1.1 g, 5 mmol). The resulting yellow-brown solution was stirred at rt for 30 min during which all of 23 was consumed according to TLC. The mixture was washed with $NH_4Cl$, sat. aq. $NaHCO_3$, and the organic layer was evaporated under reduced pressure to a brown gum. This residue was subjected to chromatography over 15 g of silica gel, eluting with 3:1 hexane-EtOAc going to 1:1 hexane-EtOAc. Evaporation of the eluant between 100 mL and 250 mL afforded 19 as a white solid (330 mg, 20%). Mp=115-116° C.; $^1$H NMR (300 MHz, $CDCl_3$) δ ppm 9.00 (s, 1H), 8.48 (s, 2H), 8.20-7.08 (m, 8H, Ar); $^{13}$C NMR (75 MHz, $CDCl_3$) δ 160.1, 156.7, 138.7, 138.1, 137.5, 132.8, 132.3, 128.9, 128.4, 128.2, 127.4, 118.4, 118.5, 80.1.

In compounds I, and III-VII, $R^1$ and $R^2$ can individually be organic groups or "radicals" that are substituted or unsubstituted, including alkyl, aryl, aralkyl cycloalkyl, cycloalkylalkyl, heterocyclyl, heterocyclylalkyl, heteroaryl, heteroarylalkyl or the like. $R^1$ and $R^2$ each can include about 1-20 carbon atoms. $R^1$ and/or $R^2$ can include double or triple bonds. $R^1$ and/or $R^2$ can also include heteroatoms.

$R^1$ and $R^2$ can each be substituted or unsubstituted as those terms are defined herein. Substituted alkyl, alkenyl, alkynyl, cycloalkyl, cycloalkylalkyl, cycloalkenyl, and cycloalkenylalkyl groups as well as other substituted groups also include groups in which one or more bonds to a hydrogen atom are replaced by one or more bonds, including double or triple bonds to a heteroatom such as, but not limited to, oxygen in carbonyl (oxo), carboxyl, ester, amide, imide, urethane, and urea groups; and nitrogen in imines, hydroxyimines, oximes, hydrazones, amidines, guanidines, and nitriles.

In general, "substituted" refers to an organic group as defined herein such as $R^1$ or $R^2$ in which one or more bonds to a hydrogen atom contained therein are replaced by one or more bonds to a non-hydrogen atom such as, but not limited to, a halogen (i.e., F, Cl, Br, and I); an oxygen atom in groups such as hydroxyl groups, alkoxy groups, aryloxy groups, aralkyloxy groups, oxo(carbonyl) groups, carboxyl groups including carboxylic acids, carboxylates, and carboxylate esters; a sulfur atom in groups such as thiol groups, alkyl and aryl sulfide groups, sulfoxide groups, sulfone groups, sulfonyl groups, and sulfonamide groups; a nitrogen atom in groups such as amines, hydroxylamines, nitriles, nitro groups, N-oxides, hydrazides, azides, and enamines; and other heteroatoms in various other groups.

Non-limiting examples of substituents that can be bonded to a substituted carbon (or other) atom include halo (F, Cl, Br, I), OR', e.g., alkoxy, OC(O)N(R')$_2$, CN, NO, NO$_2$, ONO$_2$, azido, haloalkyl, haloalkoxy, e.g., OCF$_3$, O (oxo), S (thiono), C(O), S(O), methylenedioxy, ethylenedioxy, N(R')$_2$, SR', SOR', SO$_2$R', SO$_2$N(R')$_2$, SO$_3$R', C(O)R', C(O)C(O)R', C(O)CH$_2$C(O)R', C(S)R', C(O)OR', OC(O)R', C(O)N(R')$_2$, OC(O)N(R')$_2$, C(S)N(R')$_2$, (CH$_2$)$_{0-2}$N(R')C(O)R', (CH$_2$)$_{0-2}$N(R')N(R')$_2$, N(R')N(R')C(O)R', N(R')N(R')C(O)OR', N(R')N(R')CON(R')$_2$, N(R')SO$_2$R', N(R')SO$_2$N(R')$_2$, N(R')C(O)OR', N(R')C(O)R', N(R')C(S)R', N(R')C(O)N(R')$_2$, N(R')C(S)N(R')$_2$, N(COR')COR', N(OR')R', C(=NH)N(R')$_2$, C(O)N(OR')R', or C(=NOR')R' wherein R' can be hydrogen or a carbon-based moiety, and wherein the carbon-based moiety can itself be further substituted.

When a substituent is monovalent, such as, for example, F or Cl, it is bonded to the atom it is substituting by a single bond. When a substituent is more than monovalent, such as O, which is divalent, it can be bonded to the atom it is substituting by more than one bond, i.e., a divalent substituent is bonded by a double bond; for example, a C substituted with O forms a carbonyl group, C=O, which can also be written as "CO", "C(O)", or "C(=O)", wherein the C and the O are double bonded. When a carbon atom is substituted with a double-bonded oxygen (=O) group, the oxygen substituent is termed an "oxo" group. When a divalent substituent such as NR is double-bonded to a carbon atom, the resulting C(=NR) group is termed an "imino" group. When a divalent substituent such as S is double-bonded to a carbon atom, the results C(=S) group is termed a "thiocarbonyl" group.

Alternatively, a divalent substituent such as O, S, C(O), S(O), or S(O)$_2$ can be connected by two single bonds to two different carbon atoms. For example, O, a divalent substituent, can be bonded to each of two adjacent carbon atoms to provide an epoxide group, or the O can form a bridging ether group, termed an "oxy" group, between adjacent or non-adjacent carbon atoms, for example bridging the 1,4-carbons of a cyclohexyl group to form a [2.2.1]-oxabicyclo system. Further, any substituent can be bonded to a carbon or other atom by a linker, such as (CH$_2$)$_n$ or (CR'$_2$)$_n$ wherein n is 1, 2, 3, or more, and each R' is independently selected.

C(O) and S(O)$_2$ groups can be bound to one or two heteroatoms, such as nitrogen, rather than to a carbon atom. For example, when a C(O) group is bound to one carbon and one nitrogen atom, the resulting group is called an "amide" or "carboxamide." When a C(O) group is bound to two nitrogen atoms, the functional group is termed a urea. When a S(O)$_2$ group is bound to one carbon and one nitrogen atom, the resulting unit is termed a "sulfonamide." When a S(O)$_2$ group is bound to two nitrogen atoms, the resulting unit is termed a "sulfamate."

Substituted ring groups such as substituted cycloalkyl, aryl, heterocyclyl and heteroaryl groups also include rings and fused ring systems in which a bond to a hydrogen atom is replaced with a bond to a carbon atom. Therefore, substituted cycloalkyl, aryl, heterocyclyl and heteroaryl groups can also be substituted with alkyl, alkenyl, and alkynyl groups as defined herein.

As to any of the $R^1$ or $R^2$ other groups described herein, which contain one or more substituents, it is understood, of course, that such groups do not contain any substitution or substitution patterns which are sterically impractical and/or synthetically non-feasible. In addition, the compounds of this disclosed subject matter include all stereochemical isomers arising from the substitution of these compounds.

By "chemically feasible" is meant a bonding arrangement or a compound where the generally understood rules of organic structure are not violated; for example a structure within a definition of a claim that would contain in certain situations a pentavalent carbon atom that would not exist in nature would be understood to not be within the claim. The structures disclosed herein, in all of their embodiments are intended to include only "chemically feasible" structures, and any recited structures that are not chemically feasible, for example in a structure shown with variable atoms or groups, are not intended to be disclosed or claimed herein.

When a substituent is specified to be an atom or atoms of specified identity, "or a bond", a configuration is referred to when the substituent is "a bond" that the groups that are immediately adjacent to the specified substituent are directly connected to each other in a chemically feasible bonding configuration.

An "acyl" group ($R^1C(O)$) as the term is used herein refers to a group containing a carbonyl moiety wherein the group is bonded, to a moiety such as a pyrimidine ring, via the carbonyl carbon atom. The carbonyl carbon atom is also bonded to $R^1$. A nicotinoyl group (pyridyl-3-carbonyl) group is an example of an acyl group within the meaning herein. Other examples include acetyl, i-butyroyl, benzoyl, phenylacetyl, pyridylacetyl, cinnamoyl, and acryloyl groups and the like.

The term "alkoxy" refers to an oxygen atom connected to an alkyl group, including a cycloalkyl group, as are defined above. Examples of linear alkoxy groups include but are not limited to methoxy, ethoxy, propoxy, butoxy, pentyloxy, hexyloxy, and the like. Examples of branched alkoxy include but are not limited to isopropoxy, sec-butoxy, tert-butoxy, isopentyloxy, isohexyloxy, and the like. Examples of cyclic alkoxy include but are not limited to cyclopropyloxy, cyclobutyloxy, cyclopentyloxy, cyclohexyloxy, and the like. An alkoxy group can include one to about 12-20 carbon atoms bonded to the oxygen atom, e.g., is ($C_1$-$C_4$)alkoxy and can further include double or triple bonds, and can also include heteroatoms. For example, an allyloxy group is an alkoxy group within the meaning herein. A methoxyethoxy group is also an alkoxy group within the meaning herein, as is a methylenedioxy group in a context where two adjacent atoms of a structures are substituted therewith.

The terms "aryloxy" and "arylalkoxy" refer to, respectively, an aryl group bonded to an oxygen atom and an aralkyl group bonded to the oxygen atom at the alkyl moiety. Examples include but are not limited to phenoxy, naphthyloxy, and benzyloxy.

The terms "halo" or "halogen" or "halide" by themselves or as part of another substituent mean, unless otherwise stated, a fluorine, chlorine, bromine, or iodine atom, preferably, fluorine, chlorine, or bromine.

A "haloalkyl" group includes mono-halo alkyl groups, poly-halo alkyl groups wherein all halo atoms can be the same or different, and per-halo alkyl groups, wherein all hydrogen atoms are replaced by halogen atoms, such as fluoro. Examples of ($C_1$-$C_4$)haloalkyl include trifluoromethyl, 1,1-dichloroethyl, 1,2-dichloroethyl, 1,3-dibromo-3,3-difluoropropyl, perfluorobutyl, and the like.

A "haloalkoxy" group includes mono-halo alkoxy groups, poly-halo alkoxy groups wherein all halo atoms can be the same or different, and per-halo alkoxy groups, wherein all hydrogen atoms are replaced by halogen atoms, such as fluoro. Examples of haloalkoxy include trifluoromethoxy, 1,1-dichloroethoxy, 1,2-dichloroethoxy, 1,3-dibromo-3,3-difluoropropoxy, perfluorobutoxy, and the like.

The term "($C_x$—$C_y$)perfluoroalkyl," wherein x<y, means an alkyl group with a minimum of x carbon atoms and a maximum of y carbon atoms, wherein all hydrogen atoms are replaced by fluorine atoms. Preferred is —($C_1$-$C_6$)perfluoroalkyl, more preferred is —($C_1$-$C_3$)perfluoroalkyl, most preferred is —$CF_3$.

The term "($C_x$-$C_y$)perfluoroalkylene," wherein x<y, means an alkyl group with a minimum of x carbon atoms and a maximum of y carbon atoms, wherein all hydrogen atoms are replaced by fluorine atoms. Preferred is —($C_1$-$C_6$)perfluoroalkylene, more preferred is —($C_1$-$C_3$)perfluoroalkylene, most preferred is —$CF_2$—.

Alkyl groups include straight chain and branched alkyl groups having from 1 to about 20 carbon atoms, and typically from 1 to 12 carbons or, in some embodiments, from 1 to 8 carbon atoms. Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, t-butyl, neopentyl, isopentyl, and 2,2-dimethylpropyl groups. As used herein, the term "alkyl" encompasses n-alkyl, isoalkyl, and anteisoalkyl groups as well as other branched chain forms of alkyl. Representative substituted alkyl groups can be substituted one or more times with any of the groups listed above, for example, halo, amino, hydroxy, cyano, carboxy, nitro, thio, alkoxy, and halogen groups.

Cycloalkyl groups are $C_3$-$C_{12}$ cyclic alkyl groups such as, but not limited to, cyclopropyl, cyclobutyl, cyclopentyl, cyclohexyl, cycloheptyl, and cyclooctyl groups. In some embodiments, the cycloalkyl group can have 3 to about 8-12 ring members, whereas in other embodiments the number of ring carbon atoms range from 3 to 4, 5, 6, or 7. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like. Cycloalkyl groups also include rings that are substituted with straight or branched chain alkyl groups as defined herein. Representative substituted cycloalkyl groups can be mono-substituted or substituted more than once, such as, but not limited to, 2,2-, 2,3-, 2,4-2,5- or 2,6-disubstituted cyclohexyl groups or mono-, di- or tri-substituted norbornyl or cycloheptyl groups, which can be substituted with, for example, amino, hydroxy, cyano, carboxy, nitro, thio, alkoxy, and halogen groups. The term "cycloalkenyl" alone or in combination denotes a cyclic alkenyl group.

Unless specifically indicated to the contrary, the cycloalkyl ring can be substituted with as many as n−1 substituents wherein n is the size of the carbocyclic ring with, for example, alkyl, alkenyl, alkynyl, amino, aryl, hydroxy, cyano, carboxy, heteroaryl, heterocyclyl, nitro, thio, alkoxy, and halogen groups, or other groups as are listed above.

(Cycloalkyl)alkyl groups, also denoted cycloalkylalkyl, are alkyl groups as defined herein in which a hydrogen or carbon bond of the alkyl group is replaced with a bond to a cycloalkyl group as defined above.

Alkenyl groups include straight and branched chain alkyl groups as defined above, except that at least one double bond exists between two carbon atoms. Thus, alkenyl groups have from 2 to about 20 carbon atoms, and typically from 2 to 12 carbons or, in some embodiments, from 2 to 8 carbon atoms. Examples include, but are not limited to vinyl, —CH═CH($CH_3$), —CH═C($CH_3$)$_2$, —C($CH_3$)═$CH_2$, —C($CH_3$)═CH($CH_3$), —C($CH_2CH_3$)═$CH_2$, butadienyl, pentadienyl, and hexadienyl among others.

Cycloalkenyl groups include cycloalkyl groups having at least one double bond between 2 carbons. Thus for example, cycloalkenyl groups include but are not limited to cyclohexenyl, cyclopentenyl, and cyclohexadienyl groups. Cycloalkenyl groups can have from 3 to about 8-12 ring members, whereas in other embodiments the number of ring carbon atoms range from 3 to 5, 6, or 7.

Cycloalkenyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like, provided they include at least one double bond within a ring. Cycloalkenyl groups also include rings that are substituted with straight or branched chain alkyl groups as defined above.

(Cycloalkenyl)alkyl groups are alkyl groups as defined above in which a hydrogen or carbon bond of the alkyl group is replaced with a bond to a cycloalkenyl group as defined above.

Alkynyl groups include straight and branched chain alkyl groups, except that at least one triple bond exists between two carbon atoms. Thus, alkynyl groups have from 2 to about 20 carbon atoms, and typically from 2 to 12 carbons or, in some embodiments, from 2 to 8 carbon atoms. Examples include, but are not limited to —C≡CH, —C≡C(CH$_3$), —C≡C(CH$_2$CH$_3$), —CH$_2$C≡CH, —CH$_2$C≡C(CH$_3$), and —CH$_2$C≡C(CH$_2$CH$_3$) among others.

The term "heteroalkyl" by itself or in combination with another term means, unless otherwise stated, a straight or branched chain alkyl group consisting of the stated number of carbon atoms and one or two heteroatoms selected from the group consisting of non-peroxide O, N(R), and S, and wherein the nitrogen and sulfur atoms may be optionally oxidized and the nitrogen heteroatom may be optionally quaternized. R can be H, alkyl, aryl, aralkyl or a suitable protecting group. The heteroatom(s) may be placed at any position of the heteroalkyl group, including between the rest of the heteroalkyl group and the fragment to which it is attached, as well as attached to the most distal carbon atom in the heteroalkyl group. Examples include: —CH$_2$—CH$_2$CH$_2$—OH, —CH$_2$—CH$_2$—NH—CH$_3$, —CH$_2$—S—CH$_2$—CH$_3$, —CH$_2$CH$_2$—S(═O)—CH$_3$, and —CH$_2$CH$_2$—O—CH$_2$CH$_2$—O—CH$_3$. Up to two heteroatoms may be consecutive, such as, for example, —CH$_2$—NH—OCH$_3$, or —CH$_2$—CH$_2$—S—S—CH$_3$.

A "heterocycloalkyl" ring is a cycloalkyl ring containing at least one heteroatom. A heterocycloalkyl ring can also be termed a "heterocyclyl," described below.

The term "heteroalkenyl" by itself or in combination with another term means, unless otherwise stated, a stable straight or branched chain monounsaturated or di-unsaturated hydrocarbon group consisting of the stated number of carbon atoms and one or two heteroatoms selected from the group consisting of non-peroxide O, N(R'), and S, and wherein the nitrogen and sulfur atoms may optionally be oxidized and the nitrogen heteroatom may optionally be quaternized. Up to two heteroatoms may be placed consecutively. Examples include —CH═CH—O—CH$_3$, —CH═CH—CH$_2$—OH, —CH$_2$—CH═N—OCH$_3$, —CH═CH—N(CH$_3$)—CH$_3$, —CH$_2$—CH═CH—CH$_2$—SH, and —CH═CH—O—CH$_2$CH$_2$—O—CH$_3$.

Aryl groups are (C$_6$-C$_{12}$) cyclic aromatic hydrocarbons that do not contain heteroatoms in the ring. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain about 6 to about 14 carbons in the ring portions of the groups. Aryl groups can be unsubstituted or substituted, as defined herein. Representative substituted aryl groups can be mono-substituted or substituted more than once, such as, but not limited to, 2-, 3-, 4-, 5-, or 6-substituted phenyl or 2-8 substituted naphthyl groups, which can be substituted with carbon or non-carbon groups such as those listed above.

Aralkyl groups are alkyl groups as defined above in which a hydrogen or carbon bond of an alkyl group is replaced with a bond to an aryl group as defined above. Representative aralkyl groups include benzyl and phenylethyl groups and fused (cycloalkylaryl)alkyl groups such as 4-ethyl-indanyl. Aralkenyl group are alkenyl groups as defined above in which a hydrogen or carbon bond of an alkyl group is replaced with a bond to an aryl group as defined above.

The term "heteroaryl" refers to a cyclic aromatic hydrocarbon containing at least one heteroatom, e.g., N, S or non-peroxide O, in the ring. Heteroaralkyl refers to a heteroaromatic ring connected to an alkyl moiety, e.g., pyrid-2-yl methyl.

All chiral, diastereomeric, racemic forms of a structure are intended, unless a particular stereochemistry or isomeric form is specifically indicated. Compounds used in the present invention can include enriched or resolved optical isomers at any or all asymmetric atoms as are apparent from the depictions, at any degree of enrichment. Both racemic and diastereomeric mixtures, as well as the individual optical isomers can be isolated or synthesized so as to be substantially free of their enantiomeric or diastereomeric partners, and these are all within the scope of the invention.

Selected substituents within the compounds described herein are present to a recursive degree. In this context, "recursive substituent" means that a substituent may recite another instance of itself or of another substituent that itself recites the first substituent. Because of the recursive nature of such substituents, theoretically, a large number may be present in any given claim. One of ordinary skill in the art of medicinal chemistry and organic chemistry understands that the total number of such substituents is reasonably limited by the desired properties of the compound intended. Such properties include, by of example and not limitation, physical properties such as molecular weight, solubility or log P, application properties such as activity against the intended target, and practical properties such as ease of synthesis.

Recursive substituents are an intended aspect of the disclosed subject matter. One of ordinary skill in the art of medicinal and organic chemistry understands the versatility of such substituents. To the degree that recursive substituents are present in a claim of the disclosed subject matter, the total number should be determined as set forth above.

A "salt" as is well known in the art includes an organic compound such as a carboxylic acid, a sulfonic acid, or an amine, in ionic form, in combination with a counterion. For example, acids in their anionic form can form salts with cations such as metal cations, for example sodium, potassium, and the like; with ammonium salts such as NH$_4^+$ or the cations of various amines, including tetraalkyl ammonium salts such as tetramethylammonium, or other cations such as trimethylsulfonium, and the like.

All patents cited herein are incorporated by reference herein as though fully set forth.

What is claimed is:

1. A method for preparing a 5-acylpyrimidine comprising:
(a) reacting a pyrimidine of formula (II):

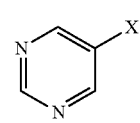

(II)

wherein X is halo or a sulfonate leaving group, and a compound of formula

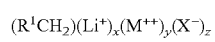

(V)

wherein R$^1$ is an organic group, M is a metal cation, each X is halo, and x, y and z are selected so that the net charge of the compound (V) is 0, wherein the coupling is carried out in the presence of an effective catalytic amount of a complexed metal, to yield a compound of formula VI;

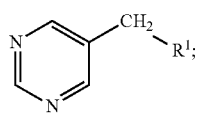

and (b) oxidizing the compound of formula (VI) to yield a 5-acylpyrimidine compound of formula (VII):

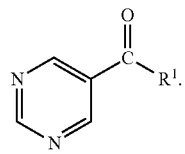

2. The method of claim 1 further comprising reacting the compound of formula VII with a solvate of the formula (Li(R²—ZnX)MgX₂)$_y$·(.ether))$_z$ wherein R² is an organic group and each X is halo, and x and y are selected so that the low-lying d-orbitals of the transition metal are filled, to yield a compound of formula (I):

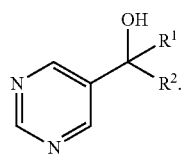

3. The method of claim 1 wherein X is halo.

4. The method of claim 3 wherein X is Br or Cl.

5. The method of claim 1 wherein M$^{++}$ in compound (V) is Zn$^{++}$ or Mg$^{++}$.

6. The method of claim 1 wherein R¹ is aryl or (substituted) aryl.

7. The method of claim 6 wherein R¹ is (substituted)phenyl.

8. The method of claim 1 wherein the metal in the complexed metal is palladium, nickel or iron.

9. The method of claim 8 wherein the metal is complexed with triphenyphosphine or acetylacetone.

10. The method of claim 9 wherein the catalyst is (Ph₃P)₄Pd, (PPh₃)₂NiCl₂ or Fe(acac)₂.

11. The method of claim 2 wherein the compound of formula (VI) is oxidized with SeO₂, KMnO₄ or CrO₃.

12. The method of claim 2 wherein the ether comprises THF or diethyl ether.

13. The method of claim 1 wherein R¹ is phenyl, 4-trifluorophenyl, 4-methoxyphenyl or 4-halophenyl or 4-trifluoromethylphenyl.

14. The method of claim 13 wherein R¹ is 4-chlorophenyl.

15. The method of claim 14 wherein R² is isopropyl, halo-substituted phenyl or cyclopropyl.

16. The method of claim 15 wherein R² is 2-chlorophenyl or 3,5-dichlorophenyl.

17. The method of claim 2 wherein R¹ is 4-trifluoromethylphenyl and R² is isopropyl.

18. The method of claim 2 wherein R¹ is 4-chlorophenyl or 4-fluorophenyl and R² is 2-chlorophenyl.

19. The method of claim 2 wherein R¹ is 4-methoxyphenyl and R² is cyclopropyl.

20. The method of claim 2 wherein R¹ is phenyl and R² is 3,4-dichlorophenyl.

* * * * *